United States Patent [19]
Smith

[11] Patent Number: 5,108,442
[45] Date of Patent: Apr. 28, 1992

[54] PROSTHETIC IMPLANT LOCKING ASSEMBLY

[75] Inventor: Todd S. Smith, Warsaw, Ind.

[73] Assignee: Boehringer Mannheim Corporation, Indianapolis, Ind.

[21] Appl. No.: 697,899

[22] Filed: May 9, 1991

[51] Int. Cl.$^5$ ............................................. A61F 2/38
[52] U.S. Cl. ......................................... 623/20; 623/18
[58] Field of Search ................... 623/16, 18, 19, 20, 623/22, 23, 38

[56] References Cited

U.S. PATENT DOCUMENTS

| | | | |
|---|---|---|---|
| D. 285,968 | 9/1986 | Kinnett | 623/20 |
| D. 285,969 | 9/1986 | Kinnett | 623/20 |
| 3,958,278 | 5/1976 | Lee et al. | 623/20 |
| 4,016,606 | 4/1977 | Murray et al. | 623/20 |
| 4,207,627 | 6/1980 | Cloutier | 623/20 |
| 4,217,666 | 8/1980 | Averill | 623/20 |
| 4,257,129 | 3/1981 | Volz | 623/20 |
| 4,470,158 | 9/1984 | Pappas et al. | 623/20 |
| 4,550,450 | 11/1985 | Kinnett | 623/20 |
| 4,673,408 | 6/1987 | Grobbelaar | 623/20 |
| 4,714,474 | 12/1987 | Brooks, Jr. et al. | 623/20 |
| 4,731,087 | 3/1988 | Sculco et al. | 623/20 |
| 4,795,468 | 1/1989 | Hodorek et al. | 623/20 |
| 4,822,362 | 4/1989 | Walker et al. | 623/20 |
| 4,944,757 | 7/1990 | Martinez | 623/20 |

FOREIGN PATENT DOCUMENTS

| | | | |
|---|---|---|---|
| 1258152 | 8/1989 | Canada | 623/18 |
| 1105198 | 7/1984 | U.S.S.R. | 623/18 |

Primary Examiner—David J. Isabella
Attorney, Agent, or Firm—Barnes & Thornburg

[57] ABSTRACT

The invention relates to a prosthetic implant assembly comprising a base component secured to a bone and a generally planar surface having a recessed portion formed therein. A spring is situated in the recessed portion of the base component and includes a tab extending away from the spring. A bearing component slidably engages the base component to couple the bearing component to the base component and the bearing is provided with an opening for receiving the tab of the spring means therein to lock the bearing component in a fixed position relative to the base component.

40 Claims, 2 Drawing Sheets

PROSTHETIC IMPLANT LOCKING ASSEMBLY

BACKGROUND AND SUMMARY OF THE INVENTION

The present invention relates to a prosthetic implant for attachment to a bone inside the body for replacing a bearing surface. More particularly, the present invention relates to a locking assembly for rigidly attaching a bearing component to a base component which has been attached to a bone.

Various methods are known in the art for securing a bearing component to a base component. One such method is disclosed in U.S. Pat. No. 4,257,129. In this device, a pin is inserted through a hole in the bearing component and into a base component. A clip member is then inserted into a slot formed in the bearing component. The clip member engages the pin to hold the bearing component in place on the base component.

U.S. Pat. No. 4,795,468 discloses another known method for locking a bearing insert to a base support of a prosthetic implant. The implant includes a resilient locking clip which is positioned in a cavity formed on one side of the base support such that when the bearing insert and the base support are assembled together, the clip extends from the cavity to lie within a groove formed on an edge of the bearing insert to secure the two components together.

Yet another method of attaching a bearing component to a base component is to compression mold the bearing component onto the base component. The bearing component cannot be removed from the base component without destruction of the bearing component. Therefore, the bearing component cannot be changed without also changing the base component.

According to the present invention, a prosthetic implant assembly is provided. The assembly includes a base component including means for securing the base component to a bone and a generally planar surface having a recessed portion formed therein. The assembly also includes spring means situated in the recessed portion of the base component. The spring means includes a tab extending away from the spring means. The assembly further includes a bearing component including means for slidably engaging the base component to couple the bearing component to the base component and means for receiving the tab of the spring means therein to lock the bearing component in a fixed position relative to the base component.

The recessed portion of the implant assembly includes a first section having a predetermined, substantially uniform depth and a second section having a depth greater than the depth of the first section. The spring means includes a spring clip having a thickness substantially equal to the predetermined depth of the first section to provide a cantilevered spring within the recessed portion. The tab extends away from an end portion of the spring clip located within the second section of the recessed portion and the means for receiving the tab includes a groove formed in a bottom surface of the bearing component for receiving the tab therein.

The assembly further includes a ramp surface formed along a side of the bearing component in close proximity to the means for receiving the tab. The ramp surface is configured to engage the tab of the spring clip and to force the tab along with a portion of the spring clip downwardly into the second section of the recessed portion as the bearing component slides relative to the base component during installation of the bearing component. The tab and the portion of the spring clip move upwardly toward the bearing component after the receiving means is situated over the tab so that the tab enters the receiving means and locks the bearing component in a predetermined position relative the base component. A hole is provided in the bearing component at a position over the spring clip to provide an access opening to permit the tab to be disengaged from the receiving means to permit removal of the bearing component from the base component.

The present invention advantageously provides an assembly for locking a bearing component to a base component which uses few parts and is easy to construct. The bearing component can be rigidly fixed to the base component, but can be easily removed. Therefore, the variety of sizes or styles of bearing components can be inserted onto the base component and inspected to determine which bearing component best fits a patient's particular needs after the base component is implanted in a bone.

BRIEF DESCRIPTION OF THE DRAWINGS

The invention may be best understood by referring to the following detailed description and drawings which illustrate the invention. The detailed description particularly refers to the accompanying figures in which.

DETAILED DESCRIPTION OF THE DRAWINGS

Figure 1:
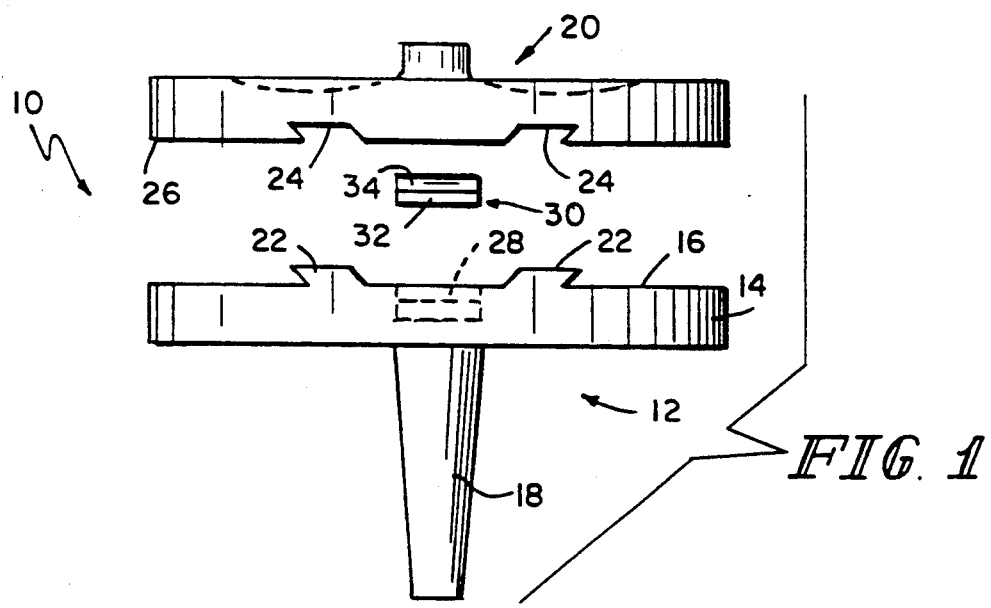
FIG. 1 is an exploded front elevational view of a preferred embodiment of the present invention illustrating a spring clip situated between a base component and a bearing component.

Referring now to the drawings, FIG. 1 illustrates the assembly 10 of the present invention. The assembly 10 includes a base component 12 for attachment to a bone (not shown). Base component 12 is illustratively a tibial tray for insertion into a tibia bone. Base component 12 includes a tray 14 having a generally planar upper surface 16 and an anchoring stem 18. Base component 12 is configured to receive a bearing component 20 thereon. Base component 12 includes a pair of spaced-apart slide members 22 which are slidably received within a pair of spaced-apart grooves 24 formed in a bottom surface 26 of bearing component 20. Base component 12 is preferably made from a metal alloy such as cobalt-chrome or titanium. Bearing component 20 is preferably made from a polymeric material such as ultra high molecular weight polyethylene (UHMWPE).

Figure 4:
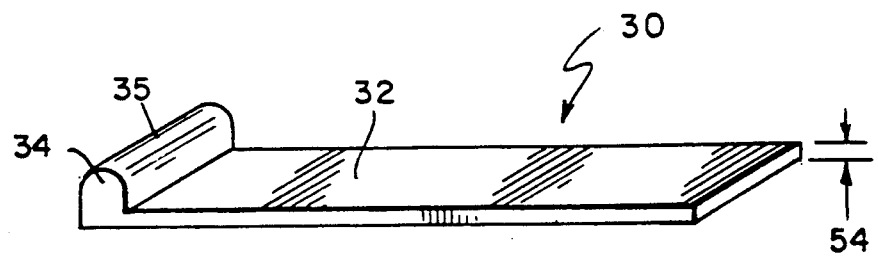
FIG. 4 is a perspective view illustrating the spring clip.

Base component 12 is formed to include a rectangularly-shaped countersink or recessed portion 28 therein between the slide members 22. Recessed portion 28 is configured to receive a spring clip 30 for locking the bearing component 20 in a fixed position relative to the base component 12. As shown in FIG. 4, spring clip 30 includes a generally planar rectangular body portion 32 and an elongated tab portion or tab 34 extending away from one end of the rectangular body portion 32 of spring clip 30. Tab 34 has a rounded upper surface 35. Spring clip 30 may be made from a variety of implantable materials. These materials include metal alloys or polymeric materials such as UHMWPE.

Figure 2:
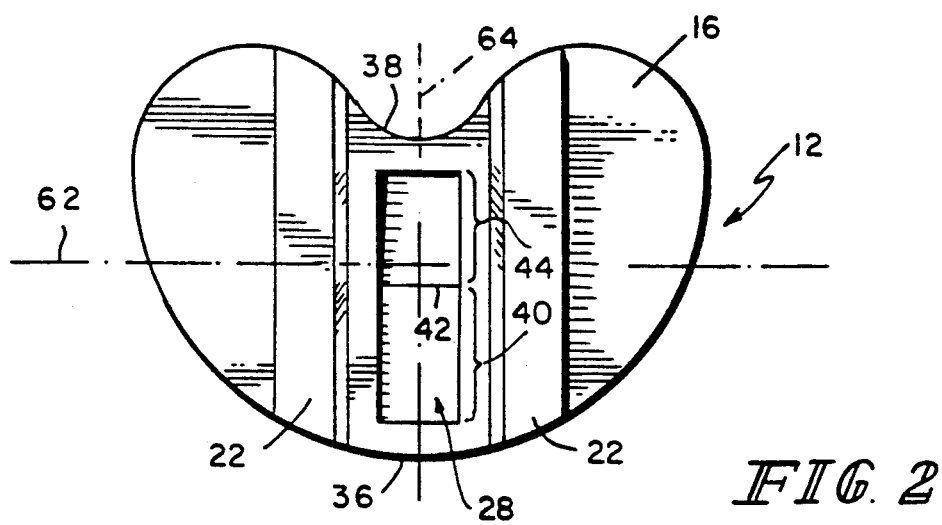
FIG. 2 is a plan view illustrating a top surface of the base component.
Figure 5:
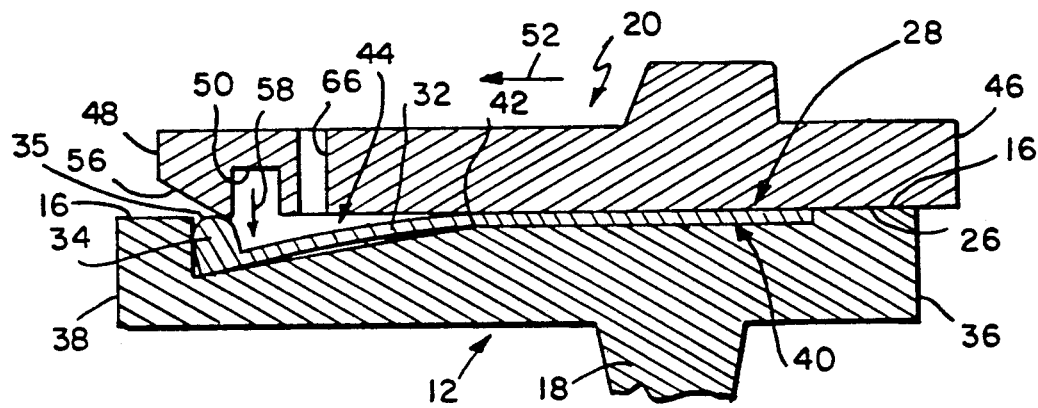
FIG. 5 is a sectional view taken through the assembly of the present invention illustrating operation of the locking assembly as the bearing component is being inserted onto the base component.
Figure 6:
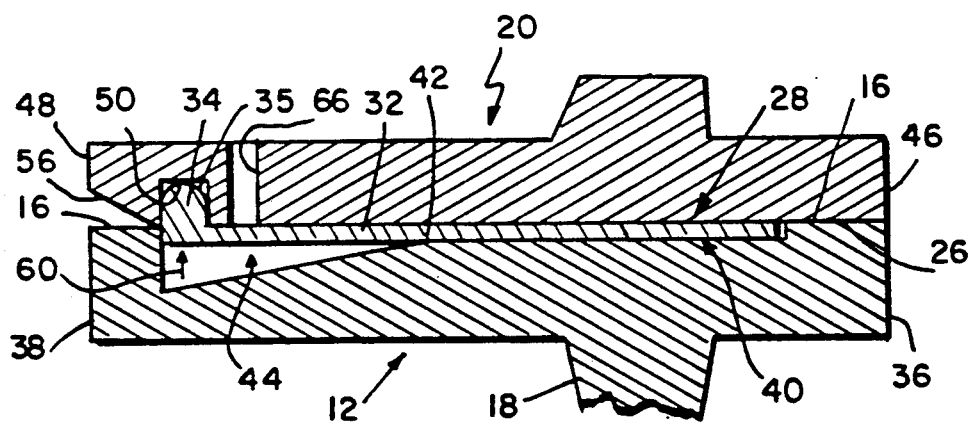
FIG. 6 is a sectional view similar to FIG. 5 illustrating the bearing component installed on the base component with the tab of the spring clip engaging a groove in the bearing component to lock the bearing component in a fixed position relative to the base component.

FIG. 2 illustrates the top surface 16 of base component 12. Base component 12 includes an anterior side 36 and a posterior side 38. Slide members 22 extend from the anterior side 36 to the posterior side 38 of base component 12. Recessed portion 28 includes an anterior first section 40 extending from a middle portion of base component 12 illustrated by dotted line 42 toward the anterior side 36 of base component 12. First section 40 has a substantially uniform predetermined depth. Recessed portion 28 also includes a posterior second section 44 extending from line 42 toward the posterior side 38 of base component 12. Second section 44 has a depth greater than the depth of the first section 40. The predetermined depth of the first section is preferably about 0.030 inches. At the middle portion 42, the depth of recessed portion 28 begins to increase to a maximum depth of about 0.100 inches at the extreme posterior end of recessed portion 28. The depths of first and second sections are best illustrated in FIGS. 5 and 6. Spring clip 30 is positioned within recessed portion 28 so that the tab 34 is situated in the second section 44 near posterior side 38 of base component 12. Tab 34 extends in a direction opposite the second section 44 of recessed portion 28.

Figure 3:
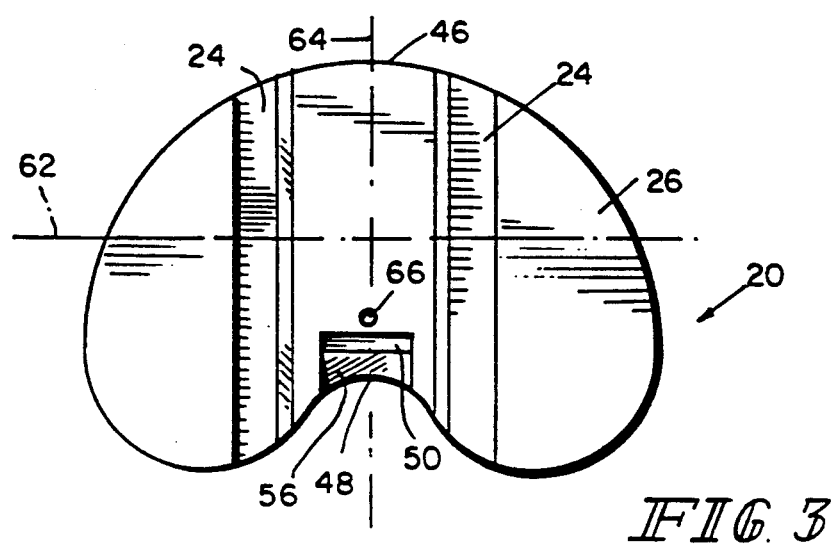
FIG. 3 is a plan view illustrating a bottom surface of the bearing component.

The tab 34 of spring clip 30 is configured to engage a groove 50 formed in bearing component 20 to lock the bearing component 20 in a fixed position relative to base component 12. Therefore, groove 50 provides the means for receiving the tab 34 of the spring means therein. As illustrated in FIG. 3, bearing component 20 includes an anterior side 46 and a posterior side 48. The groove 50 extends in a medial/lateral direction along bearing component 20 at a location near posterior side 48. Grooves 24 for engaging slide members 22 of base component 12 extend from the anterior side 46 to the posterior side 48 of bearing component 20. It will be seen that slide members 22 and grooves 24 are shaped at an angle, inclined, or dovetailed such that, when the slide members are fully engaged in the grooves, the bearing component 20 is held downwardly on the base component 12.

Operation of the assembly 10 of the present invention is best illustrated in FIGS. 5 and 6. After stem 18 has been inserted into a bone (not shown) to secure base component 12 to the bone, bearing component 20 is inserted onto base component 12 by sliding the grooves 24 of bearing component 20 over the slide members 22 of base component 12. The posterior side 48 of grooves 24 of bearing component 20 are inserted onto the slide members 22 near the anterior side 36 of base component 12. The bearing component 20 slides relative to the base component 12 over slide members 22 in a direction of arrow 52 (FIG. 5). The rectangular body portion 32 of spring clip 30 has a thickness illustrated by dimension 54 in FIG. 4. Thickness 54 is substantially equal to the predetermined depth of the first section 40 of recessed portion 28. Therefore, thickness 54 is preferably about 0.030 inches. Because spring clip 32 has about the same thickness as the depth of the first section 40 of recessed portion 28, the top surface of the rectangular portion 32 lies generally within the plane of the upper surface 16 of base component 12 and the surface of first section 40 supports the spring clip 30. Spring clip 30 provides a cantilevered spring member inside recessed portion 28 because the second section 44 of recessed portion 28 is deeper than the first section 40 and therefore does not contact the spring clip 30. Spring clip 30 can be secured within the first section 40 of recessed portion 28 if desired by welding, brazing, riveting, or sintering the spring clip within the second first section at a position near anterior side 36 of base component 12. Otherwise, the spring clip 30 can simply be placed within the recessed portion 28 without any permanent attachment.

Bearing component 20 includes a tapered or ramp-shaped surface 56 extending between the posterior end 48 of bearing component 20 and the groove 50. As bearing component 20 moves in the direction of arrow 52 shown in FIG. 5, ramp surface 56 engages the tab 34 of spring clip and forces the tab 34 in the direction of arrow 58 into the second section 44 of recessed portion 28. Second section 44 is deep enough that tab 34 can be forced in the direction of arrow 58 until the top of tab 34 is in a position even with the planar surface 16. After bearing component 20 is fully inserted onto base component 12 as illustrated in FIG. 6, tab 34 of spring clip 30 springs upwardly in the direction of arrow 60 as spring body 32 returns to its generally planar orientation so that the tab 34 enters groove 50 formed in bearing component 20.

Slide members 22 on base component 12 and grooves 24 on bearing component 20 prevent movement of bearing component 20 relative to base component 12 along a medial/lateral axis 62 shown in FIGS. 2 and 3 and along a vertical axis because of their inclination discussed above. Spring clip 30 is trapped in recessed portion by bottom surface 26 of bearing component 20 so that spring clip 30 cannot move relative to the base component 12 or bearing component 20. Therefore, by entering and engaging groove 50 in bearing component 20, tab 34 prevents movement of bearing component 20 relative to base component 12 along an anterior/posterior axis 64.

A hole or access opening 66 is provided in bearing component 20 near groove 50 at a location situated over spring clip 30. Opening 66 permits a tool (not shown) to be inserted through opening 66 to engage spring clip 30 and press spring clip 30 downwardly into second section 44 of recessed portion 28 to disengage tab 34 from groove 50. This permits removal of bearing component 20 from base component 12. Therefore, bearing component 20 can be exchanged or replaced after it has been installed onto base component 12.

Although the invention has been described in detail with reference to a certain preferred embodiment, variations and modifications exist within the scope and spirit of the invention as described and defined in the following claims.

What is claimed is:
1. A prosthetic implant assembly comprising
   a base component including means for securing the base component to a bone and a generally planar surface having a recessed portion formed therein,
   spring means situated in the recessed portion of the base component, the spring means including a tab extending away from the spring means, and a bearing component including means for slidably engaging the base component to couple the bearing component to the base component and means for receiving the tab of the spring means therein to lock the bearing component in a fixed position relative to the base component.

2. A prosthetic implant assembly comprising
a base component including means for securing the base component to a bone and a generally planar surface having a recessed portion formed therein,
spring means situated in the recessed portion of the base component, the spring means including a tab extending away from the spring means, and
a bearing component including means for slidably engaging the base component to couple the bearing component to the base component and means for receiving the tab of the spring means therein to lock the bearing component in a fixed position relative to the base component, wherein the recessed portion includes a first section having a predetermined, substantially uniform depth and a second section having a depth greater than the first depth of the section, and the spring means includes a spring clip having a thickness substantially equal to the predetermined depth of the first section, the spring clip being situated in the recessed portion to provide a cantilevered spring.

3. The assembly of claim 2, wherein the predetermined depth is about 0.03 inches and the maximum depth of the second section is about 0.1 inches.

4. The assembly of claim 2, wherein the tab extends away from an end portion of the spring clip located within the second section of the recessed portion and the means for receiving the tab includes a groove formed in a bottom surface of the bearing component for receiving the tab therein.

5. The assembly of claim 4, wherein the spring clip includes a rectangularly shaped body portion.

6. The assembly of claim 1, further comprising a hole formed in the bearing component at a position situated over the spring means, the hole providing an access opening to permit the tab to be disengaged from the receiving means of the bearing component so that the bearing component may be removed from the base component.

7. A prosthetic implant assembly comprising
a base component including a generally planar surface having a recessed portion formed therein, the recessed portion including a first section having a predetermined, substantially uniform depth below the generally planar surface and a second section having a depth greater than the depth of the first section below the generally planar surface,
a spring clip situated in the recessed portion of the base component, the spring clip including a body portion having a thickness substantially equal to the predetermined depth of the first section of the recessed portion to provide a cantilevered spring within the recessed portion, the spring clip having a tab extending away from the body portion in a direction opposite the recessed portion, and
a bearing component including means for slidably engaging the base component and means for receiving the tab of the spring clip therein to lock the bearing component in a fixed position relative to the base component.

8. The assembly of claim 7, wherein the means for receiving the tab includes a groove formed in a bottom surface of the bearing component for receiving the tab of the spring clip therein.

9. The assembly of claim 7, further comprising a hole formed in the bearing component at a position situated over the spring clip to provide an access opening to permit the tab to be disengaged from the receiving means so that the bearing component may be removed from the base component.

10. The assembly of claim 7, wherein the spring clip is rigidly fixed to the first section of the recessed portion.

11. The assembly of claim 7, further comprising a ramp surface formed along a side of the bearing component in close proximity to the means for receiving the tab, the ramp surface being configured to engage the tab of the spring clip to force the tab and a portion of the spring clip into the second section of the recessed portion as the bearing component slides relative to the base component during installation, the tab and the portion of the spring clip moving toward the bearing component after the receiving means is situated over the tab so that the tab enters the receiving means to lock the bearing component in a fixed position relative to the base component.

12. A prosthetic implant assembly comprising
a base component having an anterior side and a posterior side, the base component including a generally planar surface, first and second spaced-apart slide members formed on the generally planar surface and extending from the anterior side to the posterior side, and a recessed portion formed in the generally planar surface between the first and second slide members, the recessed portion including a first section having a predetermined, substantially uniform depth below the generally planar surface and a second section having a depth greater than the depth of the first section below the generally planar surface,
a spring clip situated in the recessed portion of the base component, the spring clip including a body portion having a thickness substantially equal to the predetermined depth of the first section of the recessed portion to provide a cantilevered spring within the recessed portion, the spring clip having a tab extending away from the body portion in a direction opposite the recessed portion, and
a bearing component including means for slidably engaging the slide members of the base component for coupling the bearing component to the base component and means for receiving the tab of the spring clip therein to lock the bearing component in a fixed position relative to the base component.

13. The assembly of claim 12, wherein the means for slidably engaging the slide members include first and second spaced-apart grooves formed in a bottom surface of the bearing component for receiving the first and second slide members, respectively, of the base component.

14. The assembly of claim 13, wherein the means for receiving the tab of the spring clip includes a third groove formed between the first and second grooves for receiving the tab therein.

15. The assembly of claim 12, further comprising a hole formed in the bearing component at a position situated over the spring clip to provide an access opening to permit the tab to be disengaged from the receiving means so that the bearing component from the base component.

16. The assembly of claim 12, wherein the spring clip is rigidly fixed to the first section of the recessed portion.

17. The assembly of claim 12, further comprising a ramp surface formed along a side of the bearing component in close proximity to the means for receiving the tab, the ramp surface being configured to engage the tab of the spring clip to force the tab and a portion of the spring clip into the second section of the recessed portion as the bearing component slides relative to the base component during installation, the tab and the portion of the spring clip moving toward the bearing component after the receiving means is situated over the tab so that the tab enters to receiving means to lock the bearing component in a fixed position relative to the base component.

18. A prosthetic implant assembly comprising
  a base component including means for securing the base component to a bone and a generally planar surface having a recessed portion formed therein,
  a flexible flat element situated in the recessed portion of the base component, the flexible flat element including a tab extending away from the flexible flat element, and
  a bearing component including means for slidably engaging the base component to couple the bearing component to the base component, the bearing element contacting the flexible flat element tab to bend the flexible flat element into an angled position as the bearing is slidingly engaging the base component and wherein the bearing component has means for receiving the tab of the spring means therein to lock the bearing component in a fixed position relative to the base component.

19. The assembly of claim 18 wherein the recessed portion includes a first section having a predetermined, substantially uniform depth and a second section having a depth greater than the first depth of the section, and the flexible flat element includes a spring clip having a thickness substantially equal to the predetermined depth of the first section, the spring clip being situated in the recessed portion to provide a cantilevered spring.

20. The assembly of claim 19, wherein the predetermined depth is about 0.03 inches and the maximum depth of the second section is about 0.1 inches.

21. The assembly of claim 19, wherein the tab extends away from an end portion of the spring clip located within the second section of the recessed portion and the means for receiving the tab includes a groove formed in a bottom surface of the bearing component for receiving the tab therein.

22. The assembly of claim 19, wherein the spring clip includes a rectangularly shaped body portion.

23. The assembly of claim 18, further comprising a hole formed in the bearing component at a position situated over the flexible flat element, the hole providing an access opening to permit the tab to be disengaged from the receiving means of the bearing component so that the bearing component may be removed from the base component.

24. A prosthetic implant assembly comprising
  a base component including means for securing the base component to a bone and a generally planar surface having a recessed portion formed therein,
  spring means situated in the recessed portion of the base component, the spring means including a tab extending away from the spring means, and
  a bearing component including means for slidably engaging the base component to couple the bearing component to the base component, means for deflecting the tab, and means for receiving the tab of the spring means therein to lock the bearing component in a fixed position relative to the base component.

25. The assembly of claim 24 wherein the means for deflecting the tab is a ramp on the bearing component.

26. The assembly of claim 24 wherein the recessed portion includes a first section having a predetermined, substantially uniform depth and a second section having a depth greater than the first depth of the section, and the spring means includes a spring clip having a thickness substantially equal to the predetermined depth of the first section, the spring clip being situated in the recessed portion to provide a cantilevered spring.

27. The assembly of claim 26, wherein the predetermined depth is about 0.03 inches and the maximum depth of the second section is about 0.1 inches.

28. The assembly of claim 26, wherein the tab extends away from an end portion of the spring clip located within the second section of the recessed portion and the means for receiving the tab includes a groove formed in a bottom surface of the bearing component for receiving the tab therein.

29. The assembly of claim 26, wherein the spring clip includes a rectangularly shaped body portion.

30. The assembly of claim 24, further comprising a hole formed in the bearing component at a position situated over the spring means, the hole providing an access opening to permit the tab to be disengaged from the receiving means of the bearing component so that the bearing component may be removed from the base component.

31. A prosthetic implant assembly comprising
  a base component including means for securing the base component to a bone and a generally planar surface having a recessed portion formed therein,
  spring means situated in the recessed portion of the base component, the spring means including a tab extending away from the spring means, and
  a bearing component including means for slidably engaging the base component to couple the bearing component to the base component such that the bearing is constrained to be fixed to the base while only permitting sliding movement relative thereto and means for receiving the tab of the spring means therein to lock the sliding movement of bearing component in a fixed position relative to the base component wherein it cannot slide relative thereto.

32. The assembly of claim 31 wherein the recessed portion includes a first section having a predetermined, substantially uniform depth and a second section having a depth greater than the first depth of the section, and the spring means includes a spring clip having a thickness substantially equal to the predetermined depth of the first section, the spring clip being situated in the recessed portion to provide a cantilevered spring.

33. The assembly of claim 32, wherein the predetermined depth is about 0.03 inches and the maximum depth of the second section is about 0.1 inches.

34. The assembly of claim 32, wherein the tab extends away from an end portion of the spring clip located within the second section of the recessed portion and the means for receiving the tab includes a groove formed in a bottom surface of the bearing component for the receiving the tab therein.

35. The assembly of claim 32, wherein the spring clip includes a rectangularly shaped body portion.

36. The assembly of claim 31, further comprising a hole formed in the bearing component at a position situated over the spring means, the hole providing an access opening to permit the tab to be disengaged from the receiving means of the bearing component so that the bearing component may be removed from the base component.

37. A prosthetic implant assembly comprising
- a base component including means for securing the base component to a bone and a generally planar surface having a recessed portion and a raised track portion formed therein,
- spring means situated in the recessed portion of the base component, the spring means including a tab extending away from the spring means, and
- a bearing component including a track engagement means for slidably engaging the base component to couple the bearing component to the base component and means on the bearing component for receiving the tab of the spring means therein to lock the sliding of the bearing component relative to the base component.

38. The assembly of claim 37 wherein a generally planar portion of the bearing component also contacts the generally planar surface of the base component.

39. The assembly of claim 37, wherein the track engagement means has at least one beveled surface which engages a beveled surface on the track portion.

40. The assembly of claim 37, wherein there are plural track portions and plural track engagement means.

* * * * *